(12) United States Patent
Mohr et al.

(10) Patent No.: US 10,854,329 B2
(45) Date of Patent: Dec. 1, 2020

(54) MOTION ESTIMATION METHOD AND APPARATUS

(71) Applicant: Canon Medical Systems Corporation, Otawara (JP)

(72) Inventors: Brian Mohr, Edinburgh (GB); Kazumasa Arakita, Utsunomiya (JP); James Matthews, Edinburgh (GB)

(73) Assignee: Canon Medical Systems Corporation, Otawara (JP)

( * ) Notice: Subject to any disclaimer, the term of this patent is extended or adjusted under 35 U.S.C. 154(b) by 141 days.

(21) Appl. No.: 16/161,134

(22) Filed: Oct. 16, 2018

(65) Prior Publication Data

US 2020/0118669 A1 Apr. 16, 2020

(51) Int. Cl.
| | |
|---|---|
| *A61B 5/00* | (2006.01) |
| *G06T 7/00* | (2017.01) |
| *G16H 30/40* | (2018.01) |
| *G16H 30/20* | (2018.01) |
| *G16H 50/20* | (2018.01) |
| *A61B 5/02* | (2006.01) |

(52) U.S. Cl.
CPC .......... *G16H 30/40* (2018.01); *A61B 5/0033* (2013.01); *G06T 7/0012* (2013.01); *G16H 30/20* (2018.01); *G16H 50/20* (2018.01); *A61B 5/02007* (2013.01)

(58) Field of Classification Search
CPC ... G06T 7/0012; G06T 7/0014; G06T 7/0016; G06T 7/20; G06T 2207/30048; G06T 2207/30101; G16H 30/40; G16H 50/20; A61B 5/02; A61B 5/02007; A61B 5/024
See application file for complete search history.

(56) References Cited

U.S. PATENT DOCUMENTS

| | | | |
|---|---|---|---|
| 8,638,999 B2 | 1/2014 | Xu et al. ................. 382/128 |
| 9,008,401 B1 | 4/2015 | Katsevich et al. .... G06T 7/0012 |
| 2009/0141935 A1 | 6/2009 | Grass et al. ............... 382/103 |
| 2009/0161933 A1 | 6/2009 | Chen ....................... 382/131 |
| 2011/0142315 A1 | 6/2011 | Hsieh et al. ............... 382/131 |
| 2015/0348261 A1 | 12/2015 | Sunami et al. ....... G06T 7/0012 |
| 2017/0262989 A1* | 9/2017 | Nempont et al. ...... A61B 6/461 |
| 2018/0040145 A1 | 2/2018 | Matthews ........... G06T 11/005 |

FOREIGN PATENT DOCUMENTS

| | | |
|---|---|---|
| JP | 2009-517113 A | 4/2009 |
| JP | 2011-507640 A | 3/2011 |
| JP | 2011-200656 A | 10/2011 |
| JP | 2016-5549 A | 1/2016 |

* cited by examiner

*Primary Examiner* — Andrew W Johns
(74) *Attorney, Agent, or Firm* — Oblon, McClelland, Maier & Neustadt, L.L.P.

(57) ABSTRACT

A medical image processing apparatus comprises processing circuitry configured to:
acquire at least one first data set representative of measurements using a medical scanner and including a representation of at least one blood vessel;
acquire a plurality of second data sets representative of measurements obtained using the medical scanner and including a representation of said at least one blood vessel, each of the plurality of second data sets representing measurements obtained for a respective different one of a plurality of cardiac phases; and
process the plurality of second data sets using a motion estimation procedure to correct for motion between the cardiac phases and, using the at least one first data set, to at least partially remove at least one feature associated with the blood vessel.

18 Claims, 5 Drawing Sheets

MOTION ESTIMATION METHOD AND APPARATUS

FIELD

The present invention relates to a method of estimating motion and removing artefacts in measurement data obtained by a medical scanner, for example cardiac scan data.

BACKGROUND

Image quality in CT scans of the heart may be affected by heart motion. Motion of the heart within the duration of a cardiac CT scan capture may result in the presence of motion artifacts in images derived from the cardiac CT scan.

Heart motion may particularly affect image quality in scans that are taken at high heart rates, for example heart rates over 60 beats per minute (bpm). Advanced scanners may obtain good image quality with moderately high heart rates, but may still see decreased quality at higher heart rates.

Scanners with a fast rotation may produce better results than scanners with a slower rotation, but motion artifacts may still be an issue even when fast rotation is used.

For some patients, drugs such as beta-blockers may be administered to slow the patient's heart rate, for example to slow the patient's heart rate below 60 beats per minute. However, beta-blockers may be contraindicated in some patients. Some patients may be unable to take beta-blockers, for example due to medical conditions.

It is known to estimate heart motion by comparing reconstructed imaging data (e.g. sets of voxels representing intensity or other parameter as a function of position in three dimensions) that is representative of different points in time, to determine motion that has occurred between the different time points. However, often the imaging data (e.g. sets of voxels) for different points in time will be reconstructed from raw scan data that includes some data in common, for example different sets of image data may be reconstructed from overlapping slices of CT scan data. This can cause inefficiencies or inaccuracies.

Furthermore, blood vessels present in an image often include associated high contrast features such as calcifications, plaque or stents that can interfere with the accurate or correct segmentation of blood vessels.

In the case of fractional flow reserve (FFR) processes or other computational fluid dynamic (CFD) processes and/or modelling processes of blood vessel or cardiac properties or function, imaging data sets are obtained for different cardiac phases (e.g. 70%, 80%, 90% and 99% phases of the cardiac cycle (e.g. RR-interval)). Accurate motion correction between the imaging data sets for the different phases can be critical for subsequent modelling processes or calculations but can sometimes be difficult to achieve.

Accurate segmentation of blood vessels for different cardiac phases is also important for fractional flow reserve (FFR) processes or other computational fluid dynamic (CFD) processes and/or modelling processes of blood vessel or cardiac properties or function. Features such as calcifications, plaque or stents can be removed from an image data set by performing registration and subtraction processes, for example by registering and subtracting non-contrast image data sets from contrast image data sets (for example data sets obtained after input of iodine or other contrast agent into the blood vessels). However, registration and subtraction processes performed on reconstructed imaging data sets can introduce additional errors or inaccuracies, and these can compound any errors or inaccuracies introduced by motion correction algorithms used on imaging data sets.

BRIEF DESCRIPTION OF THE DRAWINGS

Embodiments are now described, by way of non-limiting example, and are illustrated in the following figures, in which:—

DETAILED DESCRIPTION

Certain embodiments provide a medical image processing apparatus comprising processing circuitry configured to:
  acquire at least one first data set representative of measurements using a medical scanner and including a representation of at least one blood vessel;
  acquire a plurality of second data sets representative of measurements obtained using the medical scanner and including a representation of said at least one blood vessel, each of the plurality of second data sets representing measurements obtained for a respective different one of a plurality of cardiac phases; and
  process the plurality of second data sets using a motion estimation procedure to correct for motion between the cardiac phases and, using the at least one first data set, to at least partially remove at least one feature associated with the blood vessel.

Certain embodiments provide a method comprising acquiring at least one first data set representative of measurements using a medical scanner and including a representation of at least one blood vessel;
  acquiring a plurality of second data sets representative of measurements obtained using the medical scanner and including a representation of said at least one blood vessel, each of the plurality of second data sets representing measurements obtained for a respective different one of a plurality of cardiac phases; and
  processing the plurality of second data sets using a motion estimation procedure to correct for motion between the cardiac phases and, using the at least one first data set, to at least partially remove at least one feature associated with the blood vessel.

Certain embodiments provide a computer program product comprising computer-readable instructions that are executable to:
  acquire at least one first data set representative of measurements using a medical scanner and including a representation of at least one blood vessel;
  acquire a plurality of second data sets representative of measurements obtained using the medical scanner and including a representation of said at least one blood vessel, each of the plurality of second data sets representing measurements obtained for a respective different one of a plurality of cardiac phases; and
  process the plurality of second data sets using a motion estimation procedure to correct for motion between the cardiac phases and, using the at least one first data set, to at least partially remove at least one feature associated with the blood vessel.

The motion estimation procedure may comprise obtaining a registration or performing a registration-based procedure.

Figure 1:
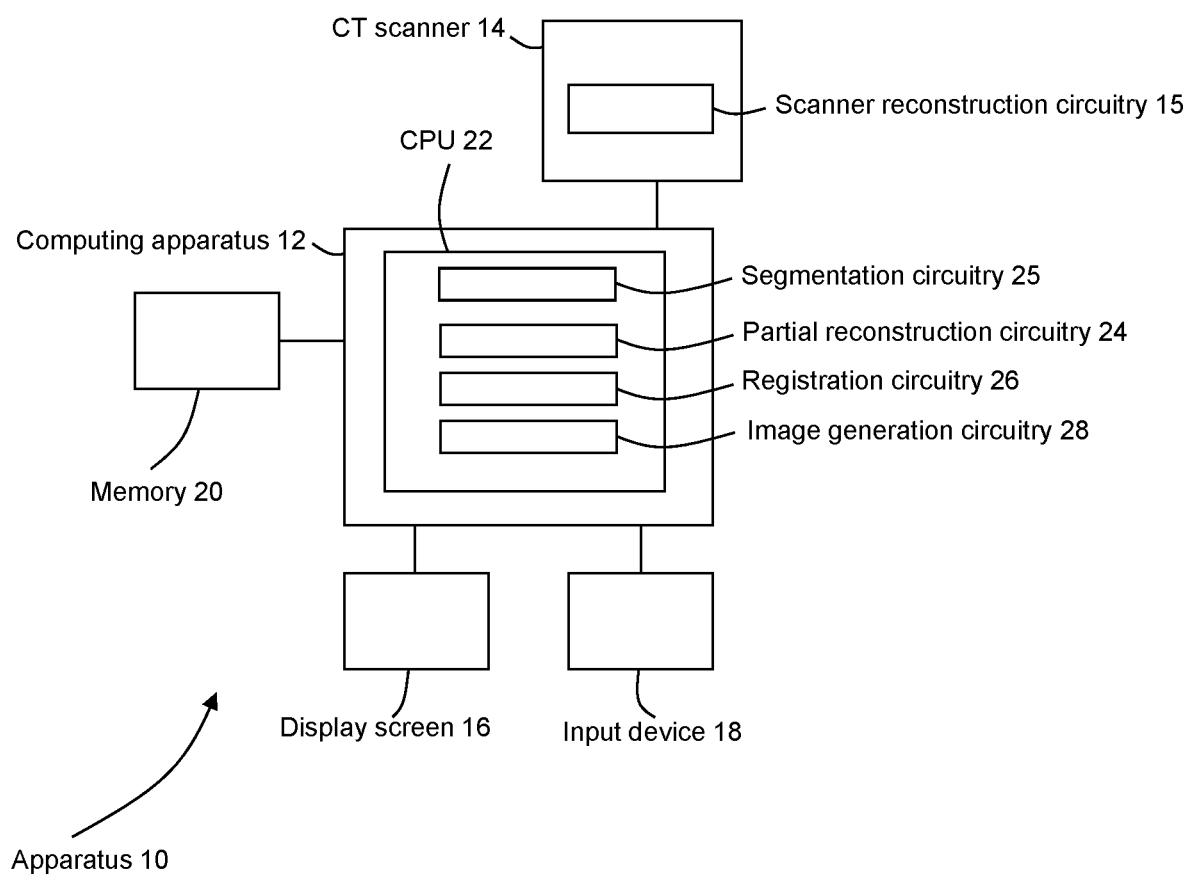
FIG. 1 is a schematic illustration of an apparatus according to an embodiment.

An imaging data processing apparatus 10 according to an embodiment is illustrated schematically in FIG. 1. The imaging data processing apparatus 10 comprises a computing apparatus 12, for example, a personal computer (PC) or workstation, which is connected to a CT scanner 14, one or more display screens 16 and an input device or devices 18, such as a computer keyboard, mouse or trackball.

The CT scanner 14 may be any CT scanner that is configured to obtain two-dimensional or three-dimensional CT scan data that is representative of a region of a patient or other subject. In the present embodiment, the region is an anatomical region comprising the heart. In other embodiments, the region may be any appropriate region. The region may comprise the brain. The region may comprise the abdomen. The region may comprise any appropriate vessel (for example, the coronary arteries) or organ (for example, the lung or liver). The region of the patient that is scanned may be referred to as a measurement volume.

The CT scanner 14 is configured to scan the region of the patient using an X-ray source and receiver mounted on a gantry. In some embodiments, a scan protocol used is a continuous volume acquisition. The gantry performs a full 360° rotation around the patient in a rotation time, which in the present embodiment is 275 ms. In some circumstances, a full rotation may be completed within a single heartbeat of the patient.

In some embodiments, each full rotation around the patient provides CT scan data that is representative of an axial slice of the region of the patient. In other embodiments, the CT scanner 14 is a multi-slice scanner configured to capture a plurality of slices in a single rotation.

In alternative embodiments, the CT scanner 14 may be replaced or supplemented by a scanner in any other imaging modality, for example a cone-beam CT scanner, MRI (magnetic resonance imaging) scanner or hybrid scanner (for example, CT-MR or CT-PET scanner) or any other suitable scanner.

In the description below, the term scan data set (for example, CT scan data set) is used to refer to raw (unreconstructed) data as may be received from a scanner. CT scan data may be representative of measurements obtained by the scanner during a CT scan, for example voltage data that is obtained by the scanner during the CT scan. A CT scan data set may comprise data that is representative of one or more axial slices. In some circumstances, a CT scan data set may be referred to as a sinogram.

A CT scan data set may comprise a plurality of subsets of data, each corresponding to a different time during a scan and therefore to a different scan angle.

In the present embodiment, CT scanner 14 comprises scanner reconstruction circuitry 15 which is configured to reconstruct CT scan data to obtain imaging data. By reconstruction, the scanner reconstruction circuitry 15 transforms the raw CT data into imaging data that comprises voxel intensities that are representative of the attenuation of X-rays at different points in space.

In the description below, the term imaging data set is used to refer to reconstructed data (which may be also referred to as imaging data). An imaging data set may comprise, for example, an array of voxels and associated intensities, with each voxel being representative of a corresponding location in the measurement volume. An imaging data set may be used to generate an image of the measurement volume, for example for display.

The CT scanner 14 may reconstruct CT scan data to obtain imaging data using any suitable method, for example filtered back-projection.

In the present embodiment, the CT scanner 14 is configured to reconstruct three imaging data sets for each axial slice of the CT scan data. In other embodiments, the CT scanner is configured to reconstruct a different number of imaging data sets for each axial slice of the CT scan data.

For each axial slice, CT scan data is obtained for a full 360° rotation of the X-ray source. Each of the three imaging data sets for a given slice is reconstructed using a respective portion of the CT scan data for that slice. Each portion comprises CT scan data from at least half of the rotation, i.e. CT scan data from at least 180° of rotation.

Each portion is offset in time, and is therefore also offset in rotation angle. For example, the three imaging data sets may be offset in time by a time corresponding to one-sixth of a rotation by the X-ray source (60° of rotation).

Data from at least 180° of rotation may be reconstructed to provide a complete reconstruction, which may be an imaging data set corresponding to an image of the entire axial slice. In some embodiments, data from an angular range of 180° plus a width of a fan beam of the scanner is reconstructed to provide a complete reconstruction. In some embodiments, references below to an angular range of 180° may be replaced with a range of 180° plus a width of a fan beam of the scanner.

In some circumstances, data from 180° of rotation may be used for parallel projections. Real CT scanners may be fan beam scanners and may use a larger range of rotational angles in reconstruction. However, some motion estimation methods and/or motion compensation methods may ignore the fan beam nature of the CT scanner and assume a parallel projection. For example, since cardiac scans may have a small field of view, the fan beam angle may be fairly small and may be close enough to parallel that good results may be achieved using parallel projection.

Each of the three imaging data sets may comprise a complete reconstruction of the axial slice, with each full reconstruction being obtained using measurements from a different range of rotation angles. Three separate images of the same axial slice may be provided, each image corresponding to a different scanning time period.

If no motion were to occur in the measurement volume during the rotation, it may be expected that each of the three imaging data sets may be substantially identical. However, the presence of motion may cause differences between the imaging data sets obtained at different times (and at different angles).

Each of the imaging data sets may comprise motion artifacts. The motion artifacts in an imaging data set may result from motion occurring during a scanning time period in which the relevant portion of the CT scan data was acquired. Motion may occur on a timescale of less than half a rotation of the scanner. For example, a shape and/or position of at least part of the heart may change between the acquisition of measurements for a first angle and the acquisition of measurements for a second angle that offset from the first angle by less than 180°.

Figure 2:
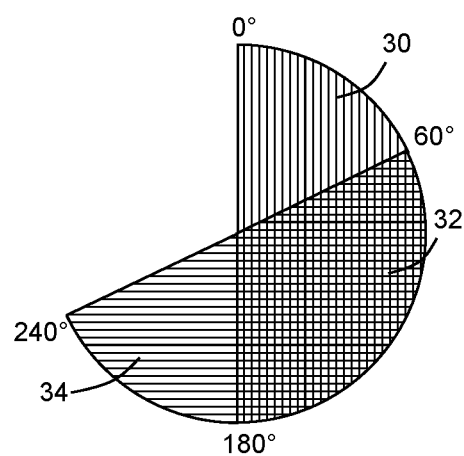
FIG. 2 is a schematic illustration of ranges of rotation angles corresponding to different images.

FIG. 2 is a schematic illustration of ranges of gantry rotation angles from which two imaging data sets A, T representative of two images of the same slice are reconstructed. A range of angles for a third imaging data set, B, representative of a third image of the same slice is not shown in FIG. 2 for clarity. First imaging data set A is reconstructed from measurements for a range of angles from 0° to 180°, which encompasses regions 30 and 32 of FIG. 2. The range of angles used to reconstruct first imaging data set A is represented using vertical hatching. Second imaging data set T is reconstructed from measurements for a range of angles from 60° to 240°, which encompasses regions 32 and 34 of FIG. 2. The range of angles used to reconstruct first imaging data set A is represented using horizontal hatching. It may be seen that measurements for a range of angles from 60° to 180° are used both in the reconstruction of first imaging data set A and in the reconstruction of second imaging data set T. In the embodiment of FIG. 2, third imaging data set B is reconstructed from measurements for a range of angles from 120° to 300° (not shown).

In the present embodiment, imaging data sets reconstructed by the CT scanner 14 (for example, A, T and B) are stored in memory 20 and subsequently provided to computing apparatus 12. In an alternative embodiment, imaging data sets are supplied from a remote data store (not shown) which may form part of a Picture Archiving and Communication System (PACS). The memory 20 or remote data store may comprise any suitable form of memory storage.

Computing apparatus 12 provides a processing resource for automatically or semi-automatically processing imaging data sets, and comprises a central processing unit (CPU) 22. In the present embodiment, the computing apparatus 12 includes partial reconstruction circuitry 24, registration circuitry 26 and image generation circuitry 28.

In the present embodiment, the partial reconstruction circuitry 24, registration circuitry 26, and image generation circuitry 28 are each implemented in computing apparatus 12 by means of a computer program having computer-readable instructions that are executable to perform the method of the embodiment. For example, the partial reconstruction circuitry 24, registration circuitry 26, and image generation circuitry 28 may each be implemented as a respective computer program or algorithm that is executable by the computing apparatus 12, for example by the CPU 22. However, in other embodiments, the various units may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 2 for clarity.

The system of FIG. 1 is configured to perform the method of an embodiment as described below with reference to FIGS. 3 and 4, in which motion compensation, registration and removal of calcium, stents, plaque or other features is performed using partial reconstructions of imaging data sets. By using partial reconstructions for these processes, in some embodiments reduced errors or improved accuracy may be obtained.

Figure 3:
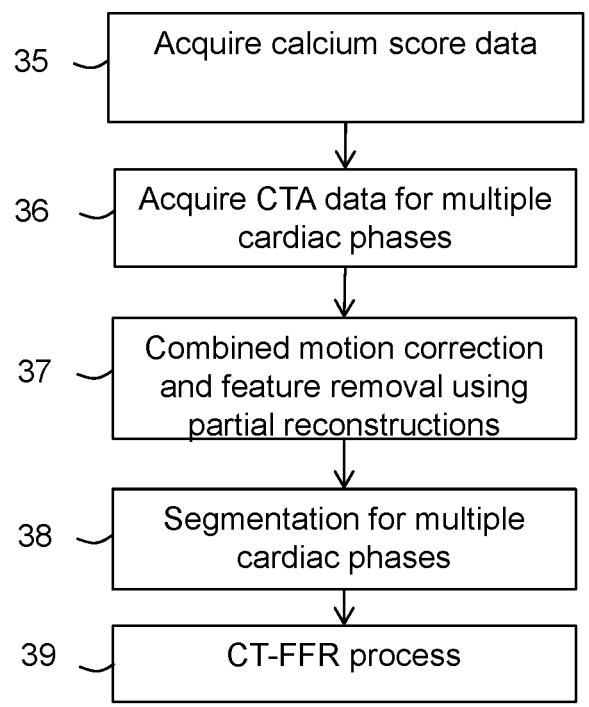
FIG. 3 is a flow chart illustrating in overview a method according to an embodiment.

The flow chart of FIG. 3 illustrates the process of the embodiment in overview. At stage 35, calcium scoring scan data such as non-contrast computed tomography (NCCT) data or other non-contrast scan data of a region of interest is acquired, for example directly from the CT scanner 14 or from a memory. In the present case, the region of interest is a region at or near the heart and including at least one cardiac blood vessel, for example an artery or vein leading from or to the heart.

At stage 36, computed tomography angiography (CTA) data, or other contrast-enhanced data, in respect of the region of interest is acquired, for example directly from the CT scanner 14 or from a memory.

In the embodiment of FIG. 3, the calcium scoring scan data is obtained by measurements on a patient or other subject using the CT scanner 14, contrast agent is then reaches or is released into the region of interest of the patient or other subject, and the CTA data is acquired. The patient or other subject usually remains within the scanner throughout these processes.

At the next stage 37, partial reconstruction data sets are obtained from the calcium scoring data and the CTA data, and combined motion correction, registration and feature subtraction processes are performed using the partial reconstruction data sets. The partial reconstruction data sets for the CTA data are obtained by omitting at least some of the raw scan data that is in common between successive CTA scan data sets, as discussed further below. Such common data cannot contribute any additional information to the motion correction process and omitting it can improve accuracy or efficiency. By using partial reconstruction data sets both for motion correction and also for registration and feature removal, further improved accuracy or efficiency can potentially be obtained.

The process of stage 37 is performed for each of several cardiac phases (for example, 70%, 80%, 90% and 99% phases in the RR interval). The raw scan data and the partial reconstruction data sets for the different cardiac phases can be obtained in any suitable manner. For example, in the present embodiment a single extended dataset is obtained that covers the desired phase interval (e.g. covering the 70%, 80%, 90% and 99% phases in the RR interval in this embodiment). This single extended dataset may cover more than 360 degrees of rotation. R to R may, for example, be about 0.8 seconds, so to cover the cardiac phase interval from 70% to 100% may require 0.35 seconds of acquisition. If the period of rotation is for example 0.275 seconds, the extended data set may cover 1.3 rotations or about 470 degrees of rotation. This single extended dataset is then divided into the partial reconstructions that are used for motion correction and subtraction. Any other suitable method to obtain the partial reconstruction data sets may be used in other embodiments. For example, there may be separate data acquisitions, and separate raw scan data sets, covering different cardiac phases or rotation intervals of interest, and the partial reconstruction data sets may be obtained by suitable processing of one or more of the different scan data sets. Alternatively or additionally, the partial reconstructions may be obtained by suitable processing of one, two or more already-reconstructed full imaging data sets.

Following the processes of stage 37 for each of the cardiac phases, fully reconstructed imaging data sets (sets of voxels or pixels) are then generated for each of the cardiac phases based on the motion-compensated data sets with features removed and the reconstructed imaging data sets for the different phases are subject to a segmentation process at stage 38 to segment the blood vessel(s) of interest.

The segmentations of the blood vessel(s) for the different cardiac phases are then used at stage 39 in a CT-FFR process or other computational fluid dynamic (CFD) process and/or modelling processes of blood vessel or cardiac properties or function, according to known techniques.

Certain features of the process of FIG. 3 are described in further detail with reference to the flow chart of FIG. 4, which illustrates schematically some of the stages of the process in additional detail.

As noted above, an important part of the process is the use of partial reconstructions for motion correction. Stages 44, 50 and 52 represent a motion correction process performed on the CTA data for each of the cardiac phases.

As noted above with reference to FIG. 2, there may be three imaging data sets (labelled A, B, T) produced for each rotation of the scanner. The data sets are used in the motion compensation process.

Beginning with one of the cardiac phases (for example 70% phase) two or more of the data sets (A, B, T) obtained at or near the 70% cardiac phase point can be used to obtain the motion compensation.

In some embodiments, motion is estimated from just two volumes R, T, producing a single warp field. The warp field may be considered to be a motion estimate, and may be used in reconstruction. In some embodiments, three imaging or more data sets are used and motion estimation may be run twice or more, or a combined motion estimation procedure may be used. Two or more warp fields are produced, which are fed into a reconstruction stage. In other embodiments, any appropriate number of imaging data sets and any appropriate number of motion estimation processes may be used.

Figure 4:
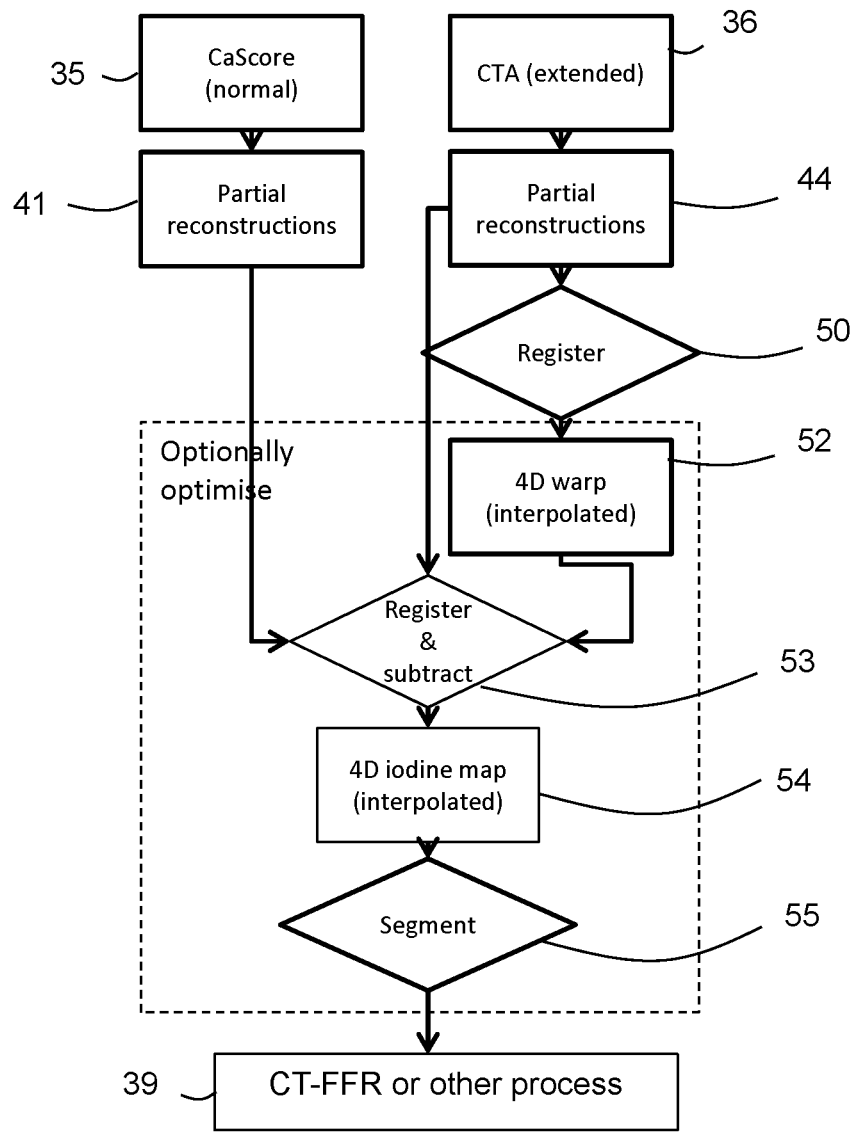
FIG. 4 is a flow chart illustrating in more detail certain features of the method of FIG. 3.

At stage 44 of the flow chart of FIG. 4, the partial reconstruction circuitry 24 receives a first imaging data set R from the memory 20. The first imaging data set has been reconstructed by the CT scanner 14 from data representative of CT measurements obtained by the CT scanner over the duration of a first scanning time period. In the first scanning time period, the gantry rotated through a first range of rotation angles (for example, 0° to 180°). In other embodiments, first imaging data set R may be received from the CT scanner 14 or from a data store, for example a remote data store.

First imaging data set R is representative of an anatomical region of a patient, which in this embodiment comprises the patient's heart. In this embodiment, first imaging data set R is representative of an axial slice through the patient's heart. First imaging data set R may be considered to be a full reconstruction for the axial slice to which it corresponds.

The partial reconstruction circuitry 24 also receives a second imaging data set T from the CT scanner 14. Second imaging data set T is representative of the same axial slice of the same region of the patient as first imaging data set R. Second imaging data set T has been reconstructed by the CT scanner 14 from data representative of CT measurements obtained by the CT scanner over the duration of a second scanning time period. During the second scanning time period, the gantry rotated through a second range of rotation angles (for example, 60° to 240°).

The first scanning time period and second scanning time period overlap. The second range of rotation angles overlaps with the first range of rotation angles.

In one embodiment the first imaging data set R is reconstructed using measurements acquired for an angular range from 0° to 180°, which corresponds to regions 30 and 32 of FIG. 2. The second imaging data set T is reconstructed using measurements acquired for an angular range from 60° to 240°, which corresponds to regions 32 and 34 of FIG. 2. Data from the range of angles from 60° to 180° (region 34) is common to imaging data sets R and T.

At stage 44 of the flow chart of FIG. 4, the partial reconstruction circuitry 24 uses the first imaging data set R to obtain a first partial reconstruction imaging data set R' that is reconstructed from data representative of measurements for the range of angles represented by region 30 of FIG. 2 (i.e., 0° to 60°). The partial reconstruction circuitry 24 uses the second imaging data set T to obtain a second partial reconstruction imaging data set T' that is reconstructed from data representative of measurements for the range of angles represented by region 34 of FIG. 3 (i.e., 180° to 240°). Data representative of measurement for the range of angles represented by region 32 of FIG. 2 (i.e., 60° to 180°) is excluded from the reconstruction of first partial reconstruction imaging data set R' and second partial reconstruction imaging data set T'.

In the embodiment described in relation to FIGS. 3 and 4, the partial reconstructions may be obtained by suitable processing of already-reconstructed full imaging data sets (e.g. a three dimensional array of voxels representing attenuation or other parameter as a function of position). One method of processing the fully reconstructed data to obtain partial reconstructions according to an embodiment is described below in relation to FIG. 5. In alternative embodiments the partial reconstruction circuitry receives scan data (e.g. raw data from the scanner as a function of scan time/rotational position) and obtains the partial reconstructions by omitting data for a selected range of angles and then performing a reconstruction process on the scan data with the selected data omitted.

Returning to FIG. 4, the output of stage 44 is the two partial reconstruction imaging data sets R', T'. At stage 50, the partial reconstruction circuitry 24 passes the first partial reconstruction imaging data set R' to the registration circuitry 26. The partial reconstruction circuitry 24 also passes the second partial reconstruction imaging data set T' to the registration circuitry 26.

At stage 50 of the method of FIG. 4, the registration circuitry 26 registers the first partial reconstruction imaging data set R' and the second partial reconstruction imaging data set T'. In the present embodiment, the registration circuitry 26 performs a non-rigid registration, for example by using the method of Piper, J et al, Objective evaluation of the correction by non-rigid registration of abdominal organ motion in low-dose 4D dynamic contrast-enhanced CT, Physics in Medicine and Biology 57(6), 1701-1715 (2012). A global non-rigid registration procedure is performed using Mutual Information as a similarity measure, and a warp field (deformation field) is computed using the Crum-Hill-Hawkes scheme (William R. Crum, Derek L. G. Hill, David J. Hawkes. Information Theoretic Similarity Measures in Non-rigid Registration, Proceedings of IPMI'2003, pp. 378-387). In the present embodiment, the warp field is a dense vector field, in which an individual displacement vector is defined for each voxel. The warp field may be a 2D or 3D vector field representing the movement of the anatomy over a given period of time. Any other suitable registration procedure may be used in alternative embodiments.

In the present embodiment, the output of stage 50 is a warp field that represents motion between a central time point of R' and a central time point of T' Note that the central time point of R' is not the same as the central time point of R, and the central time point of T' is not the same as the central time point of T'. For example, in the case of a 90° overlap, the warp field represents motion between a point 45° before the central time point of R and a point 45° after the central time point of T (or vice versa, depending on whether R or T was scanned first).

The warp field may be considered to be representative of motion between the first scanning time period for which R is obtained and the second scanning time period for which T is obtained (taking into account that no motion information is obtained for the overlap in time between the first scanning time period and second scanning time period). The warp field may be considered to be an estimate of motion. In other embodiments, any suitable estimate of motion may be obtained from the registering of R' and T'.

It may be seen from FIG. 2 that the range of angles represented by region 32 of FIG. 2 is common to imaging data sets R and T. It may be considered that there is no useful motion information to be gained by registering the data in imaging data sets R and T that is representative of the range of angles in region 32 (in this embodiment, 60° to 180°).

Therefore, in this embodiment, a first partial reconstruction R' is obtained that is representative of a range of angles that are only part of imaging data set R (and not part of imaging data set T) and a second partial reconstruction T' is obtained that is representative of a range of angles that are only part of imaging data set T (and not part of imaging data set R). The partial reconstructions from data in these ranges of angles (regions 30 and 34) may be considered to contain all the data in R and T that provides real, or non-redundant or non-duplicate, motion information. The ranges of angles (regions 30 and 34) are consistently 180°, and therefore may be considered to represent the same spatial region.

In some circumstances, partial reconstructions R', T' may have poor (and very directional) spatial resolution, but may contain almost the same motion information as the original volumes R, T from which they were derived.

In some circumstances, a more accurate estimation of motion may be obtained by registering partial reconstructions R' and T' than may have been obtained by registering complete reconstructions R and T. Since volumes R and T are reconstructed from overlapping regions of the scan data (for example, sinogram data), parts of the volume data of R and T may be highly correlated. In some circumstances, registration of R and T may tend to over- or under-estimate motion. The over- or under-estimation of motion may depend on the orientation of image detail. The over- or under-estimation of motion may be difficult to predict. Furthermore, it may be difficult to perform a registration in the presence of motion artifacts.

Although description has been provided above of performing motion registration at stages 44, 50 and 52 using partial reconstructions of two successive data sets, in practice at stages 44, 50 and 52 more than two successive data sets may be used and multiple registrations or multi-data set registration processes may be used. The output at stage 52 may then be a 4D or time-dependent warp field that represents motion compensation as a function of time.

The processes of stages 40, 50 and 52 are performed for each of the multiple cardiac phases (e.g. 70%, 80%, 90% and 99% phases) and time-dependent motion compensation (warp field) information is obtained for each of the cardiac phases. The processes of stages 40, 50 and 52 for the multiple cardiac phases may be performed in a single combined stage or process in some embodiments. The single combined stage or process may comprise multiple registrations (or even a single groupwise registration or some other time and space regularised registration) the output of which is a 4D warp representing both space and time parameters.

Turning to stages 35 and 41, it is a feature of the method of FIG. 4 that partial reconstruction(s) of calcium score data (or other non-contrast data) is used to remove features associated with the blood vessels that can interfere with accurate segmentation (for example, calcifications, stents or plaque).

At stage 35, the calcium score data is acquired, as mentioned above. At stage 41, appropriate partial reconstructions of the calcium score data are obtained for use in a registration and subtraction process.

Partial reconstructions of the calcium score data may be obtained for one of the cardiac phases (e.g. the 70% phase) or for each of the cardiac phases (e.g. each of the 70%, 80%, 90% and 99% phases).

The calcium score data may be obtained from a scan during a full 360 degree or more rotation. The partial reconstruction data from the CTA scan may be aligned with data obtained from such calcium score data (for example a partial reconstruction data set starting from a particular angle e.g. 60 degrees is registered to the calcium score data also starting at the same angle e.g. 60 degrees.) Usually, the registered partial volumes should have the same range of rotation. In some embodiments it may be desired to obtain the calcium score data for approximately the same range of the R to R phase as for the CTA data, although in practice in some embodiments the calcium score data may not cover the entire 70% to 100% phase interval.

The partial reconstructions of the calcium score data may be obtained by performing the same or similar processes as used at stage 44 to obtain the partial reconstructions of the CTA data. For example, for each partial reconstruction of the calcium score data scan data for the same range of angles as for the CTA data may be omitted and then the remaining data may be used to generate the partial reconstruction.

For each of the cardiac phases, the one or more partial reconstructions of the calcium score data obtained at stage 41, the partial reconstructions of the CTA data 44 and the warp field obtained at stage 52 are then provided to the registration circuitry 26. At stage 53 the registration circuitry performs a registration process to align the partial reconstruction(s) of the calcium score (or other non-contrast enhanced) data and the corresponding partial reconstruction (s) of the CTA data (which is suitably motion-compensated using the determined warp field(s)). The subtraction process is then performed with respect to the aligned data to remove features represented in the contrast-enhanced (e.g. CTA) and non-contrast enhanced (e.g. calcium score) partial reconstruction data sets.

The output of the stage 53 is a set of representations of the contrast agent as a function of position for each of the cardiac phases (e.g. the each of the 70%, 80%, 90% and 99% phases). Taken together the set of representations provide a 4D representation showing the change in position and concentration of the contrast agent between the cardiac phases and thus as a function of time.

The image generation circuitry 28 performs reconstructions of data sets that are representative of measurements of the measurement volume, subject to subtraction and motion compensation processes. In the process of reconstruction, the reconstruction circuitry 28 uses the estimated motion warp field 52 to compensate for motion that occurred during the capture of the measurements. The reconstruction using the estimated motion may be performed using, for example, the method of Tang et al, A combined local and global motion estimation and compensation method for cardiac CT, Proc. SPIE 9033, Medical Imaging 2014: Physics of Medical Imaging, 903304 (19 March 2013).

At stage 55, resulting fully reconstructed imaging data sets representing the contrast agent (e.g. having been subjected to the motion compensation, feature removal and reconstruction processes) for each of the cardiac phases of interest are passed to segmentation circuitry 25 to perform a segmentation process to segment the blood vessel(s) of interest.

The segmented data sets for the different cardiac phase are then processed at stage 39 to perform a fractional flow reserve (FFR) processes according to known technique. Any other suitable process, for example any suitable computational fluid dynamic (CFD) process and/or a modelling process of blood vessel or cardiac properties or function may be performed at stage 39.

In a variant of the process of FIG. 4 (indicated by the dashed box in FIG. 4) optionally the motion compensation, registration and feature removal (e.g. subtraction) processes may be optimised or modified in dependence on one more output of the processes. Thus, the correction for motion and the at least partial removal of the at least one feature may be subject to at least one constraint derived from the reconstructed image data set(s) and/or subject to a constraint of optimising a value of at least one parameter derived from the reconstructed image data set(s).

For example a subtraction goodness parameter may be determined that provides a metric that is optimised when, for example, pixel or voxel values of the data set(s) are always positive (within expected noise limits).

Similarly, a lumen segmentation parameter may be calculated based on data sets following the subtraction process, which has value(s) that depend on whether the determined lumen (e.g. blood vessel) segmentation is consistent with one or more predetermined geometrical, anatomical or other constraints. For example if the lumen segmentation parameter value (s) is too high or low this may suggest that the lumen shape, size or path is not consistent with what may be expected from normal human or other anatomy.

The parameter values or other constraints may be included as inputs to the motion compensation, registration and feature removal (e.g. subtraction) processes such that the processes are adjusted until acceptable values of the parameter(s) are obtained and/or the constraint(s) are satisfied.

As described above, according to embodiments partial reconstructions are used to determine an estimate of motion compensation and then full motion-compensated reconstructions of the image data may be obtained. Any suitable process for obtaining the partial reconstructions and for generating the full motion-compensated reconstruction (e.g. set of voxels) of an image may be used.

In the embodiment of FIGS. 3 and 4, by way of example the set of data that is reconstructed in respect of imaging data set T is the discrete Fourier transform (DFT) of imaging data set T that was obtained when the process of FIGS. 3 and 4 was applied to the imaging data set. In other embodiments, any suitable data may be used.

In the present embodiment, the reconstruction circuitry 28 divides the angular range of the data for imaging data set T (for example 60° to 240°) into 12 regions, each comprising a respective angular range of 15° (corresponding to a time of about 12 ms). In other embodiments, any number of regions may be used.

The reconstruction circuitry 28 obtains a respective partial reconstruction of the DFT data for each of the 12 regions. Each partial reconstruction may be referred to as a partial image. Each partial image may have good spatial resolution in one direction and very poor spatial reconstruction in other directions. Each partial image may have better temporal resolution than a full reconstruction image of the DFT of T would have.

A respective time is associated with each of the partial reconstructions. For example, a partial reconstruction may be reconstructed from data representative of measurements acquired over a time period (for example, a time period of around 12 ms), and the time associated with that partial reconstruction may be a time of a midpoint of the data acquisition.

The reconstruction circuitry 28 interpolates the warp field 52 to the time associated with each of the partial reconstructions. The reconstruction circuitry 28 obtains 12 interpolated warp fields, each of which may be different.

In the present embodiment, the interpolation comprises using a cubic function with additional parameters added to adjust the interpolation. In the present embodiment, the warp field is set to zero at the middle of the target volume. In other embodiments, any method of interpolating the estimate of motion may be used.

For each of the partial reconstructions, the reconstruction circuitry 28 transforms the partial reconstruction in accordance with the interpolated warp field that was obtained by interpolating the warp field 52 to a time associated with that partial reconstruction.

The reconstruction circuitry 28 then adds together the transformed partial reconstructions to obtain a further imaging data set.

Thus, in embodiments, the complete reconstruction of an image T is adjusted in dependence on the estimate of motion by obtaining multiple partial reconstructions of T, interpolating the warp field 52 to the different times of the different partial reconstructions, applying the interpolated warp field to transform the different partial reconstructions, and then combining the transformed partial reconstructions. By applying the estimate of motion to the reconstruction, motion effects may be reduced.

In some embodiments, the reconstruction may be a reconstruction of all the CT data obtained for a single axial slice to obtain a final image. The motion estimate may be used to adjust the reconstruction geometry.

The further imaging data set may be a data set from which some motion effects have been removed. Some motion artifacts may be reduced when compared with motion artifacts in at least one of the imaging data sets R, T. For example, fewer motion artifacts may be present in the new volumetric imaging data set than in the target phase data set T, or the severity of motion artifacts may be reduced when compared with those in target phase data set T.

The method of FIG. 4 may be performed for each axial slice in a volumetric CT data set. In some embodiments, the method of FIG. 4 may be performed for a multi-slice volume obtained from a multi-slice scanner.

In some embodiments, the CT scanner 14 reconstructs three imaging data sets (for example, T, A and B) which are received and processed by the computing apparatus 12 to obtain an estimate of motion. In other embodiments, any number of imaging data sets may be reconstructed from the volumetric CT data, each corresponding to a different time point. For example, a target phase data set and one, three, four or five data sets for other, different phases may be reconstructed from the CT data.

The method described above with reference to FIG. 4 may be used to produce reconstructed data sets with reduced motion artifacts. The method of FIG. 4 may provide an improved estimation of coronary artery motion. By reducing motion artifacts, it may be possible to improve image quality without increasing the speed of rotation of the CT scanner.

In the embodiment described above with reference to FIGS. 3 and 4, the computing apparatus 12 receives imaging data sets (for example, R and T), and processes the imaging data sets to obtain partial reconstruction imaging data sets (for example, R' and T').

Figure 5:
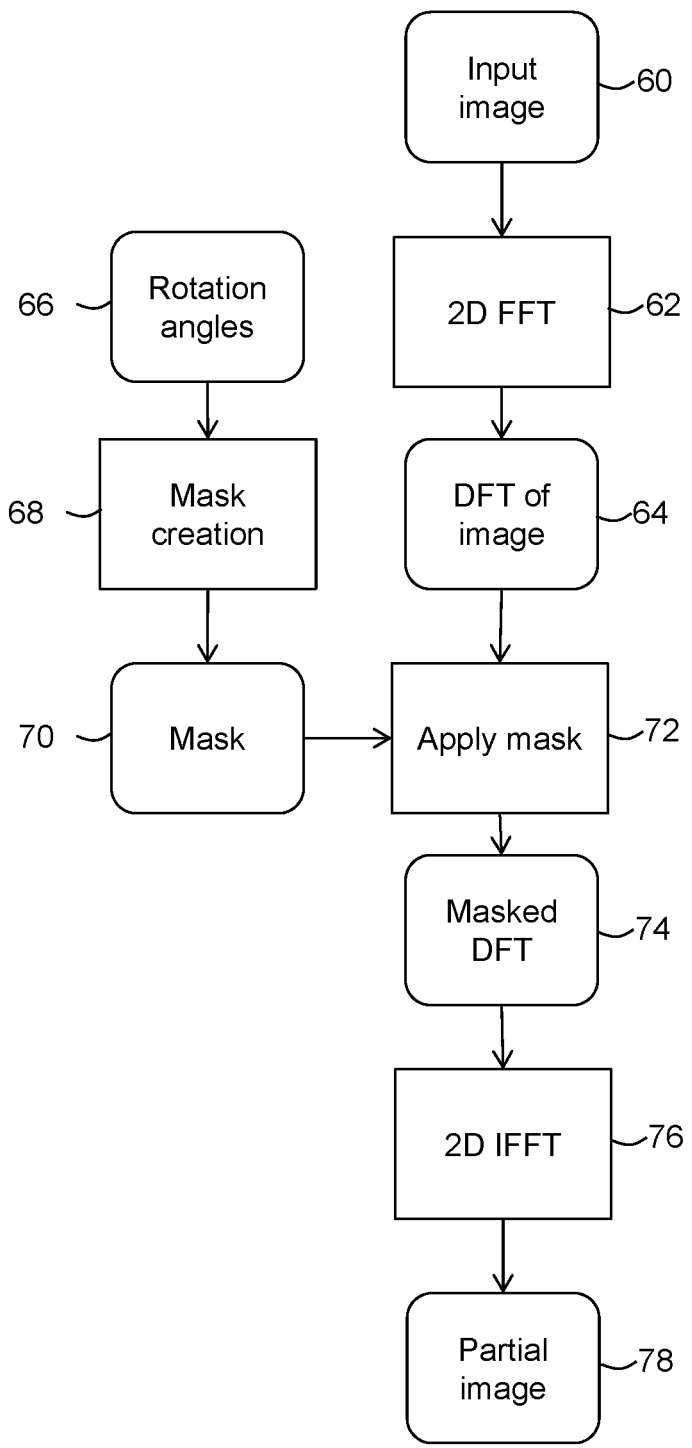
FIG. 5 is a flow chart illustrating in overview a method of obtaining partial reconstructions for use in embodiments.

FIG. 5 is a flow chart illustrating in overview one method of obtaining a partial reconstruction (for example, R') from a complete reconstruction (for example, R).

In the present embodiment, the partial reconstruction circuitry 24 has obtained imaging data set R (represented as input image 60 in FIG. 5) from the CT scanner 14. In some embodiment the partial reconstruction circuitry 24 may not have access to the CT scan data from which the CT scanner reconstructed imaging data set R.

At stage 62, the partial reconstruction circuitry 24 processes the imaging data set R to obtain data that is representative of measurements obtained by the scanner during the first scanning time period. In the present embodiment, the partial reconstruction circuitry 24 processes the imaging data set R by performing a two-dimensional fast Fourier transform (FFT) to produce a discrete Fourier transform (DFT) 64 of the imaging data set R. In other embodiments, any suitable processing method may be used.

Due to the central slice theorem, radial angles of the DFT 64 may correspond to gantry angles. Data that lies along a line passing through the origin of the DFT 64 at a given radial angle may be representative of measurement data acquired at a corresponding gantry angle. The DFT 64 is a transformed image slice that is capable of being created either by taking a 2D DFT of the reconstructed image (as performed at stage 62) or by taking a one-dimensional DFT of each line of the sinogram (raw CT scan data) and overlaying the 1D DFT results at appropriate radial angles through the centre of an image. Therefore, a line through the centre of the DFT 64 corresponds to a particular line of the sinogram (and therefore corresponds to a particular gantry angle).

The partial reconstruction circuitry 24 also receives from memory 20 (or from the CT scanner 14, or from another data store) ranges of rotation angles 66 comprising the range of rotation angles represented by imaging data set R (in this embodiment, 0° to 180°) and the range of rotation angles represented by imaging data set T (in this embodiment, 60° to 240°). The rotation angles 66 are used to determine which parts of the DFT 64 to mask out. The rotation angles 66 may also be used in reconstruction stage 56.

At stage 68, the partial reconstruction circuitry 24 creates a mask 70 for masking out a part of the DFT 64 of R that is representative of angles that are common to R and T (in this embodiment, 60° to 180°). Stage 68 may be performed before, after, or concurrently with stage 64.

The mask 70 may be used to create partial reconstructions by masking out parts of the Fourier transform of each image slice. Since each radial line through the DFT 64 corresponds to a particular line of the sinogram (CT scan data), masking out a radial line of the DFT 64 corresponds to removing the information contributed by that line of the sinogram. The masking may be considered to eliminate data for overlapping parts of a sinogram that is representative of measurements for the appropriate angles, leaving information from parts of the sinogram that contain motion information. The mask 70 may be configured to select lines passing through the origin of the DFT 74 at radial angles corresponding to a desired time period.

At stage 72, the partial reconstruction circuitry 24 applies the mask 70 to the DFT 64 of imaging data set R to obtain a masked DFT 74. The masked DFT comprises only data corresponding to measurements for angles that are included in R but are not included in T.

By applying an appropriate mask to the Fourier transform of the image R, the partial reconstruction circuitry 24 may be considered to remove information from the range of gantry rotation angles for which R and T overlap, which may leave only angles where there is motion information. Data in the range from 60° to 180° is no longer included.

At stage 76, the partial reconstruction circuitry 24 performs a two-dimensional inverse fast Fourier transform (IFFT) of the masked DFT 74 to obtain a partial reconstruction imaging data set R' (which in FIG. 5 is referred to as partial image 78).

The partial reconstruction imaging data set R' may have better temporal resolution than the imaging data set R from which it was obtained, at the expense of reduced spatial resolution in one axis. The axis having reduced spatial resolution may be an axis from which no useful motion information may have been obtained if R and T were to be registered, due to the overlap in data between R and T.

The method of FIG. 5 is also performed on imaging data set T to obtain a partial reconstruction imaging data set T', which is representative of measurements obtained for angles included in T but not in R (which in this embodiment are angles from 180° to 240°).

In other embodiments, a different method from that described above with reference to FIG. 5 may be used to obtain partial reconstruction imaging data sets R', T' from imaging data sets R, T. For example, in some embodiments, the partial reconstruction circuitry 24 performs a projection of an imaging data set, masks the resulting projection data using the rotation angles, and then performs a back-projection to obtain a partial reconstruction imaging data set. In other embodiments, any suitable method may be used. For example, in some embodiments a similar result may be achieved by convolution of the imaging data set with a highly anisotropic kernel.

Each of the partial reconstruction imaging data sets R', T' is representative of a range of angles that is less than 180° (hence the imaging data set being a partial, rather than a full, reconstruction). The angles for R' (region 30) are directly opposite the angles for T' (region 34). The angles for R' are offset by 180° from the angles for T'.

In other embodiments, the computing apparatus 12 receives raw scan data (for example, CT scan data) from the scanner 14 and processes the raw scan data. The computing apparatus 12 selects parts of the scan data that are to be used in reconstructing partial reconstruction imaging data sets R', T'. In some embodiments, the computing apparatus 12 reconstructs partial reconstruction imaging data sets R', T' without first performing any complete reconstruction (for example, without reconstructing imaging data sets R, T).

Referring again to the exemplary angles of FIG. 2, in one embodiment the partial reconstruction circuitry 24 receives a set of scan data, and selects a portion of the scan data comprising measurements obtained in angular range 30 (0° to 60°). The scan data in angular range 30 is data that was obtained during a first scanning time period (the time taken to scan from 0° to 180°) but not during a second scanning time period (the time taken to scan from 60° to 240°). The partial reconstruction circuitry 24 reconstructs a partial reconstruction imaging data set R' from the selected portion of the scan data.

The reconstruction circuitry 24 selects a portion of the scan data comprising measurements obtained in angular range 34 (180° to 240°). The scan data in angular range 30 is data that was obtained during a second scanning time period (the time taken to scan from 60° to 240°) but not during a first scanning time period (the time taken to scan from 0° to 180°). The partial reconstruction circuitry 24 reconstructs a partial reconstruction imaging data set T' from that selected portion of the scan data.

The registration circuitry 26 obtains an estimate of motion from the partial reconstruction imaging data sets R', T' and the image generation circuitry 28 reconstructs an imaging data set that is a complete reconstruction of scan data for the axial slice, for example using the method described above with reference to FIG. 4.

In further embodiments, the scanner reconstruction circuitry 15 of the scanner 14, instead of the partial reconstruction circuitry 24, reconstructs parts of the scan data to obtain the partial reconstruction imaging data sets R', T'. In some embodiments, the scanner 14 passes the partial reconstruction imaging data sets to computing apparatus 12. In further embodiments, some or all of the process of FIG. 4 is performed in the scanner 14 or in any suitable apparatus.

In the present embodiment, the scanner acquires CT data and reconstructs that CT data to provide imaging data. In other embodiments, the scanner acquires data of any suitable modality (for example, CT, cone-beam CT, MR, PET, SPECT, X-ray or ultrasound) and uses a reconstruction method suitable for reconstructing imaging data sets from data of the acquired modality. The scanner may reconstruct data from the scanner to provide any appropriate two-dimensional or three-dimensional imaging data sets. In some embodiments, the scanner is a hybrid scanner (for example, a CT-MR or CT-PET scanner) and the method of FIG. 2 is applied to the CT portion of data from the hybrid scanner.

In some embodiments, the scanner is a cone-beam CT scanner. In some embodiments, the imaging data sets are angiography imaging data sets. Cone-beam CT may have a slower rotation speed than some other CT scan methods. In some circumstances, a cone-beam CT scanner may experience some unwanted movement (for example a wobbling movement) during rotation. In some cone-beam CT embodiments, more than two registrations are performed when estimating motion, to obtain a more detailed model of movement over time.

The measurement volume may be any appropriate anatomical region of any human or animal subject, for example the abdominal region. The anatomical region may comprise any suitable anatomical structure, for example any organ (for example, heart, brain, lung or liver) or vessel (for example, coronary artery).

Certain embodiments provide a medical imaging method comprising creating partial reconstructions from NCCT and CTA data, registering the CTA reconstructions to produce a motion field as a function of time, and registering the CTA reconstructions to the NCCT and subtracting to produce an iodine or other contrast agent map as a function of time.

Partial reconstructions may be computed by determining the range of time periods that do not overlap with the time period within the acquisition window (information not shared between reconstructions).

The partial reconstructions may be determined by computing the 2D discrete Fourier transformation (DFT) of each image of each dataset, applying a mask that selects only lines passing through the origin of each DFT image at radial angles corresponding to the time period determined, and computing the 2D inverse DFT of the resulting masked images.

Segmentation (such as, for example, coronary vessel segmentation) may be performed using the iodine or other contrast agent map to produce a segmentation as a function of time.

Fully reconstructed volumes may be produced using the motion field.

The motion field and/or the iodine (or other contrast agent) map function may be interpolated, for example according to a parameterisation.

The parameterisation may be optimised (optionally along with effects on all inputs) according to some score.

The score may comprise a subtraction goodness score. A constraint may comprise that values in subtraction are positive within noise and/or some combination with segmentation consistency. A constraint may comprise that iodine (or other contrast agent) map and subtraction values are consistent with motion field.

Certain embodiments provide a medical image processing apparatus comprising: processing circuitry configured to: acquire first data including a calcified area inside a blood vessel and plurality of second data including angiography for each cardiac phase, correct a cardiac phase data included in the plurality of the second data to subtract the calcified area and correct a motion of the blood vessel, based on the first data and the plurality of the second data.

The processing circuitry may be further configured to: calculate a degree of movement of the blood vessel between the plurality of cardiac phases based on data of a difference period in which the data collection period differs among the plurality of second data, and correct the motion of the cardiac phase data based on the degree of movement.

The data for calculating the degree of movement may be calculated by subtracting the second data which was obtained during the difference period and the first data which was obtained during the difference period.

Certain embodiments provide a medical image processing apparatus comprising: processing circuitry configured to: acquire first data including a characteristic area inside a blood vessel and plurality of second data including angiography for each cardiac phase, correct a cardiac phase data included in the plurality of the second data to subtract the characteristic area and correct a motion of the blood vessel, based on the first data and the plurality of the second data.

Certain embodiments provide a medical image processing apparatus comprising: processing circuitry configured to: acquire: first data including a calcified area of a blood vessel obtained during a first period, second data including angiography area obtained during a second period which is shorter than the first period, wherein the second period overlaps all the period with the first period, third data including angiography area obtained during a third period which is shorter than the first period, wherein the third period overlaps all the period with the first period and overlaps at least partially with the second period. The processing circuitry may be configured to identify a fifth period which is a prior period within a period excluding a overlapping period of the second period and the third period, a sixth period which is a later period within a period excluding a overlapping period of the second period and the third period. The processing circuitry may be configured to calculate first subtraction data obtained by subtracting the second data obtained during the fifth period with the first data obtained during the fifth period, second subtraction data obtained by subtracting the third data obtained during the sixth period with the second data obtained during the sixth period, and third subtraction data obtained by subtracting the first subtraction data with the second subtraction data. The processing circuitry may be configured to calculate a degree of movement between the second data and the third data based on the third subtraction data. The processing circuitry may be configured to reconstruct an image based on the degree of the movement.

The processing circuitry may be further configured to: acquire fourth data including angiography area obtained during a fourth period which is shorter than the first period, wherein the fourth period overlaps all the period with the first period and overlaps at least partially with the third period. The processing circuitry may be further configured to identify a seventh period which is a prior period within a period excluding an overlapping period of the third period and the fourth period, and an eighth period which is a later period within a period excluding an overlapping period of the third period and the fourth period.

The processing circuitry may be further configured to calculate fourth subtraction data obtained by subtracting the third data obtained during the seventh period with the first data obtained during the seventh period, fifth subtraction data obtained by subtracting the fourth data obtained during the eighth period with the first data obtained during the eighth period, and sixth subtraction data obtained by subtracting the fourth subtraction data with the fifth subtraction data.

The processing circuitry may be further configured to calculate a second degree of movement between the third data and the fourth data based on the sixth subtraction data.

The processing circuitry may be further configured to reconstruct an image based on the degree of the movement and the second degree of movement.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus comprising processing circuitry configured to:
    acquire at least one first data set representative of measurements using a medical scanner and including a representation of at least one blood vessel;
    acquire a plurality of second data sets representative of measurements obtained using the medical scanner and including a representation of said at least one blood vessel, each of the plurality of second data sets representing measurements obtained for a respective different one of a plurality of cardiac phases; and
    process the plurality of second data sets using a motion-estimation procedure to correct for motion between the cardiac phases and, using the at least one first data set, to at least partially remove at least one feature associated with the blood vessel.

2. Apparatus according to claim 1, wherein the processing circuitry is configured to calculate an amount of movement of the at least one blood vessel between the plurality of cardiac phases based on data of a difference period in which a data collection period differs among the plurality of second data sets.

3. Apparatus according to claim 1, wherein the processing circuitry is configured to obtain partial reconstructions of the second data sets, and the motion estimation procedure is performed using the partial reconstructions of the first data sets.

4. Apparatus according to claim 3, wherein the processing circuitry is further configured to obtain a partial reconstruction of the at least one first data set and the motion estimation procedure is performed using the partial reconstructions of the second data sets and the partial reconstruction of the at least one first data set.

5. Apparatus according to claim 1, wherein one of the plurality of second data sets is representative of measurements of a measurement volume obtained by rotation of the medical scanner relative to the measurement volume during a first scanning time period;
    a further one of the plurality of second data sets is representative of measurements of the measurement volume obtained by rotation of the medical scanner relative to the measurement volume during a second scanning time period that overlaps the first scanning time period; and
    the processing circuitry is configured to:
    perform a procedure to calculate an amount of movement between the first scanning time period and second scanning time period based at least on said one of the second data sets and said further one of the second data sets, excluding from said one of the second data sets and said further one of the second data sets at least some of the data representative of said measurements obtained during an overlap between the first scanning time period and second scanning time period.

6. Apparatus according to claim 1, wherein the processing of the data comprises determining a warp field that represents an amount of movement and using said warp field to correct for motion.

7. Apparatus according to claim 1, wherein the processing comprises performing a subtraction process to subtract a representation of the at least one first data set from a representation of one or more of the second data sets to at least partially remove said at least one feature associated with the blood vessel.

8. Apparatus according to claim 1, wherein the at least one feature associated with the blood vessel comprises at least one of a calcification, a stent, plaque.

9. Apparatus according to claim 1, wherein the motion estimation procedure comprises performing at least one of a registration-based procedure, a non-rigid registration.

10. Apparatus according to claim 1, wherein the processing circuitry is further configured to reconstruct at least one image data set using the plurality of second data sets subject to said correction of motion and said removal of at least one feature associated with the blood vessel.

11. Apparatus according to claim 10, further comprising performing a segmentation process to segment said at least one blood vessel in said at least one reconstructed data set.

12. Apparatus according to claim 10, wherein the correction for motion and the at least partial removal of the at least one feature are subject to at least one constraint derived from the reconstructed image data set.

13. Apparatus according to claim 10, wherein the correction for motion and the at least partial removal of the at least one feature are performed subject to a constraint of optimising a value of at least one parameter derived from the reconstructed image data set.

14. Apparatus according to claim 1, wherein the processing circuitry is further configured to perform a fractional flow reserve (FFR) process using the plurality of second data sets after processing the second data sets to obtain said correction of motion and said removal of at least one feature associated with the blood vessel.

15. Apparatus according to claim 1, wherein the at least one first data set comprises at least one non-contrast enhanced data set, and the plurality of second data sets comprises a plurality of contrast-enhanced data sets.

16. Apparatus according to claim 1, wherein the at least one first data set comprises at least one data set obtained from a calcium scoring scan, and the plurality of second data sets are obtained from a coronary angiography scan.

17. A method comprising acquiring at least one first data set representative of measurements using a medical scanner and including a representation of at least one blood vessel;
acquiring a plurality of second data sets representative of measurements obtained using the medical scanner and including a representation of said at least one blood vessel, each of the plurality of second data sets representing measurements obtained for a respective different one of a plurality of cardiac phases; and
processing the plurality of second data sets using a motion estimation procedure to correct for motion between the cardiac phases and, using the at least one first data set, to at least partially remove at least one feature associated with the blood vessel.

18. A non-transitory computer-readable medium storing computer instructions that are executable to:
acquire at least one first data set representative of measurements using a medical scanner and including a representation of at least one blood vessel;
acquire a plurality of second data sets representative of measurements obtained using the medical scanner and including a representation of said at least one blood vessel, each of the plurality of second data sets representing measurements obtained for a respective different one of a plurality of cardiac phases; and
process the plurality of second data sets using a motion estimation procedure to correct for motion between the cardiac phases and, using the at least one first data set, to at least partially remove at least one feature associated with the blood vessel.

* * * * *